US011529131B1

(12) United States Patent
Chambers et al.

(10) Patent No.: US 11,529,131 B1
(45) Date of Patent: Dec. 20, 2022

(54) SURGICAL RETRACTOR

(71) Applicant: Government of the United States as Represented by the Secretary of the Air Force, Wright-Patterson AFB, OH (US)

(72) Inventors: James A Chambers, Falls Church, VA (US); Kenneth P Seastedt, Alexandria, VA (US); Jocelyn Raymundo-Grinstead, JB Andrews, MD (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 307 days.

(21) Appl. No.: 16/803,024

(22) Filed: Feb. 27, 2020

(51) Int. Cl.
*A61B 17/02* (2006.01)
*B33Y 80/00* (2015.01)
*A61B 17/00* (2006.01)

(52) U.S. Cl.
CPC .......... *A61B 17/0206* (2013.01); *B33Y 80/00* (2014.12); *A61B 2017/00526* (2013.01); *A61B 2017/00915* (2013.01); *A61B 2017/00955* (2013.01)

(58) Field of Classification Search
CPC ... A61B 17/02; A61B 17/0206; A61B 17/025; A61B 17/0293; A61B 17/0218; B33Y 80/00
See application file for complete search history.

(56) References Cited

U.S. PATENT DOCUMENTS

| | | | | |
|---|---|---|---|---|
| 4,616,633 A * | 10/1986 | Vargas Garcia | ....... | A61B 17/02 600/206 |
| 5,431,153 A * | 7/1995 | Lee | ................ | A61B 17/320036 606/191 |
| 2011/0257478 A1 * | 10/2011 | Kleiner | ................ | A61B 1/0607 600/104 |
| 2014/0277659 A1 * | 9/2014 | Kumar | ............... | G05B 19/4097 700/117 |
| 2017/0196578 A1 * | 7/2017 | Zubrod | .............. | A61B 18/1442 |
| 2018/0271602 A1 * | 9/2018 | Frey | ........................ | A61B 34/10 |

* cited by examiner

*Primary Examiner* — Christopher J Beccia
(74) *Attorney, Agent, or Firm* — AFMCLO/JAZ; James F. McBride

(57) ABSTRACT

The systems and methods provided herein are directed to a surgical retractor which is optimized for production by additive manufacturing systems in situations where external medical supplies are interrupted or unavailable.

6 Claims, 6 Drawing Sheets

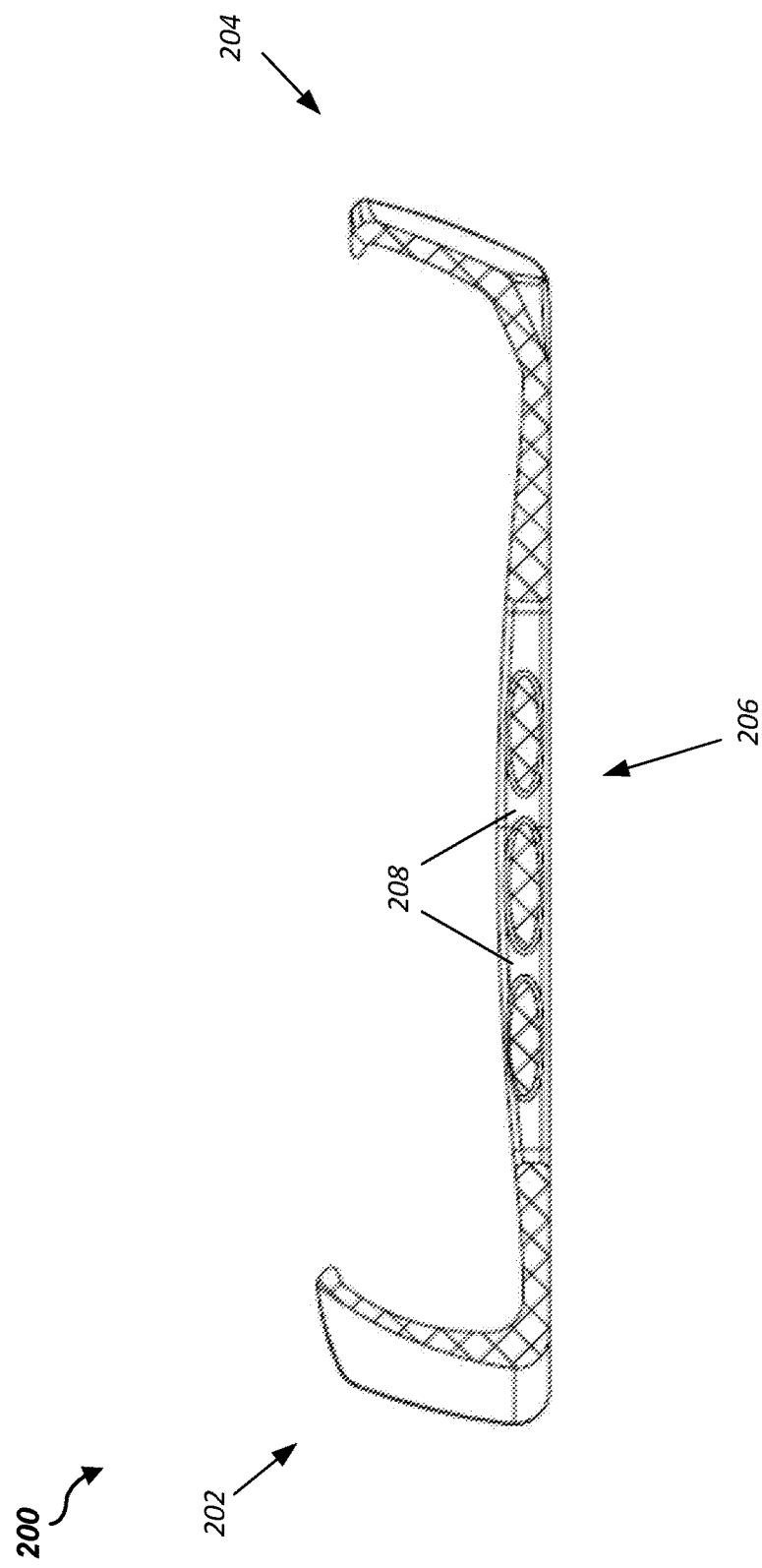

SURGICAL RETRACTOR

STATEMENT OF GOVERNMENT INTEREST

The invention described herein may be manufactured and used by or for the Government of the United States for all governmental purposes without the payment of any royalty.

BACKGROUND AND BRIEF DESCRIPTION

Worldwide, a variety of medical facilities are forced to operate under difficult conditions, still working to provide optimal care to patients. These conditions can include unreliable access to supplies from external sources, which is traditionally mitigated by assuring a plentiful and varied inventory of needed devices and supplies on-site.

Additive manufacturing (AM), also known as three-dimensional (3D) printing, offers another method to mitigate unpredictable loss of external supple sources. AM technology provides the potential ability to regenerate stocked items as well as modify them or even create novel products de novo.

A surgical retractor is described that can be 3D printed in a reasonable time using a commercially-available desktop-sized 3D printer.

BRIEF DESCRIPTION OF DRAWINGS

The novel features believed to be characteristic of the disclosure are set forth in the appended claims. In the descriptions that follow, like parts are marked throughout the specification and drawings with the same numerals, respectively. The drawing FIGURES are not necessarily drawn to scale and certain FIGURES can be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIG. 6 is a cross-section view of the surgical retractor of FIGS. 4 and 5.

DESCRIPTION OF THE DISCLOSURE

The description set forth below in connection with the appended drawings is intended as a description of exemplary embodiments of the disclosure and is not intended to represent the only forms in which the present disclosure can be constructed and/or utilized. The description sets forth the functions and the sequence of blocks for constructing and operating the disclosure in connection with the illustrated embodiments. It is to be understood, however, that the same or equivalent functions and sequences can be accomplished by different embodiments that are also intended to be encompassed within the spirit and scope of this disclosure.

Generally described, the systems and methods herein are directed to the use of a desktop-sized three-dimensional printing device to construct a surgical retractor that is able to be sterilized and suitable for medical use. The retractor has parallel arms representing swept wings allowing for an easy toe-in motion, and also arm configuration to facilitate instrumentation at angles, such as drilling. One side is small enough to accommodate most orthopedic incisions, and the other is large enough to be useful in a number of soft tissue operative cases.

Figure 1:
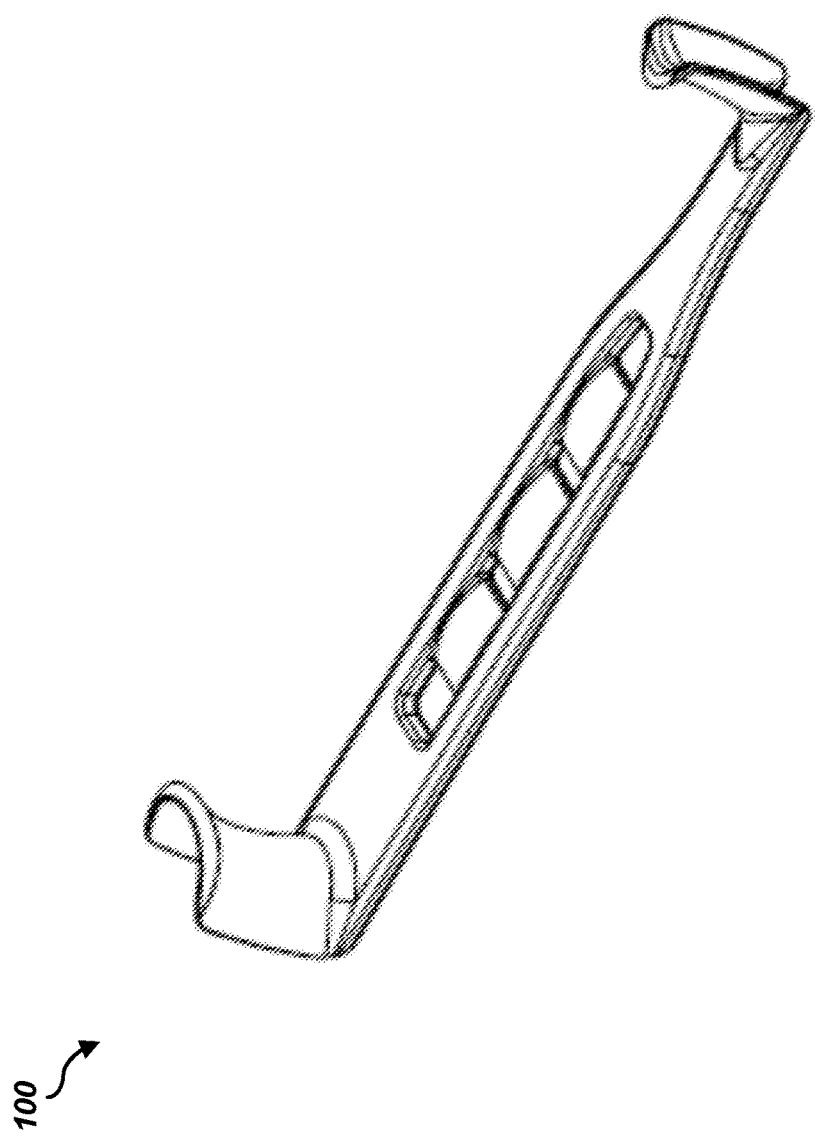
FIG. 1 is perspective view of a surgical retractor made of metal.

FIG. 1 shows a surgical retractor 100 with a structure and dimensions tailored for a construction of stainless steel. In one implementation, the retractor 100 is made of martensitic precipitation-hardened steel of approximately 17% chromium and 4% nickel, known in the art as 17-4 PH steel. In one embodiment, the steel is vacuum heat treated to 1900° F. for between 1 and 2 hours; allowed to cool at a rate of 25-35° F. per minute to below 90° F.; vacuum heat treated a second time at 1150° F. for approximately 4 hours; and then again allowed to cool to under 200° F. One of ordinary skill will recognize that varying these treatments can affect the properties of the resulting structure. Furthermore, other grades and compositions of metal are known in the art, with factors such as hardness, malleability, and density varying according to the chosen materials. If a stronger or more flexible device is needed, either the materials or the treatments can be adjusted accordingly.

In some implementations, the treated metal surfaces may be finished to a roughness of 63 Ra or better. Depending on the intended use of the surgical retractor, particular standards may need to be met for the surface properties of the device. Notably, the entire retractor 100 is cast as a single solid piece. As shown, it includes no movable sections, joints, or separate components, and therefore requires no joining, fastening, or welding in order to construct. A retractor 100 can be produced in its entirety by a commercially-available desktop AM device.

Figure 2:
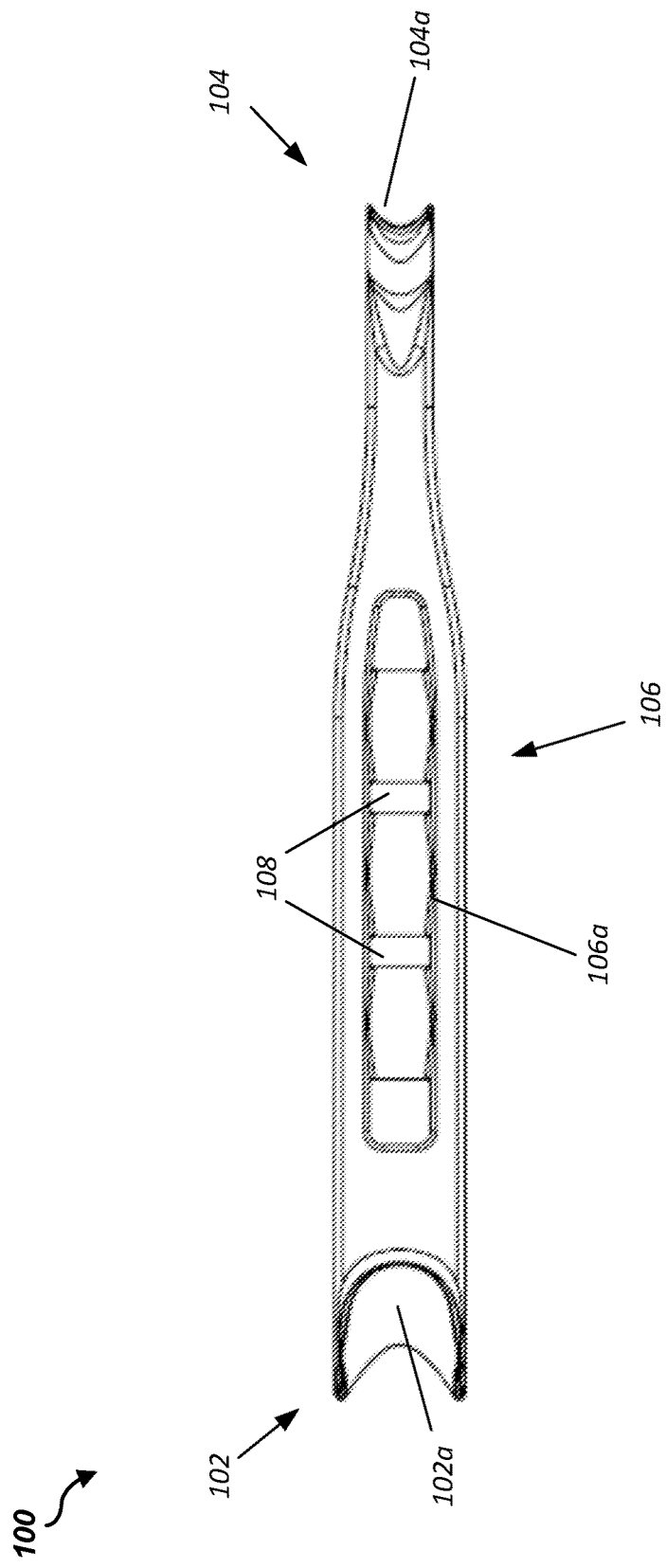
FIG. 2 is a plan view of the surgical retractor of FIG. 1.

FIG. 2 shows a plan view of the surgical retractor 100. As shown, the retractor 100 has a total length of 9.0 inches and a maximum width (found at the wider end 102) of 1.0 inches. Its narrower end 104 has a width of approximately 0.50 inches.

As shown, the body of the retractor 100 includes a body portion 106 with a central hollow 106a in which a plurality of support bars 108 are disposed. The hollow section 106 is approximately 4.2 by 0.48 inches and follows the contour of the retractor. The support bars 108 are formed of solid steel with an oval cross section that is 0.24 inches across at its broadest, each bar 108 extending the full width of the hollow 106a. Collectively, the hollow 106a and support bars 108 serve multiple functions. First, the existence of a hollow section in the center of the retractor reduces the total visual area occluded by the retractor, so that it is less likely the retractor will need to be re-positioned to inspect something below it. Additionally, the support bars 108 are shaped and sized to allow purchase, either by fingers or by a grasping tool, so that the surgical retractor 100 can be adjusted and/or relocated.

Both ends 102 and 104 are shaped with a concave groove (102a and 104a respectively) to allow surgical tools, such as drills, to rest thereon. In some implementations, one or both of the grooves 102a, 104a may be explicitly shaped to accommodate particular tools whose size and shape are known. Multiple models of retractor 100, each accommodating different tools, may be printed as needed.

Figure 3:
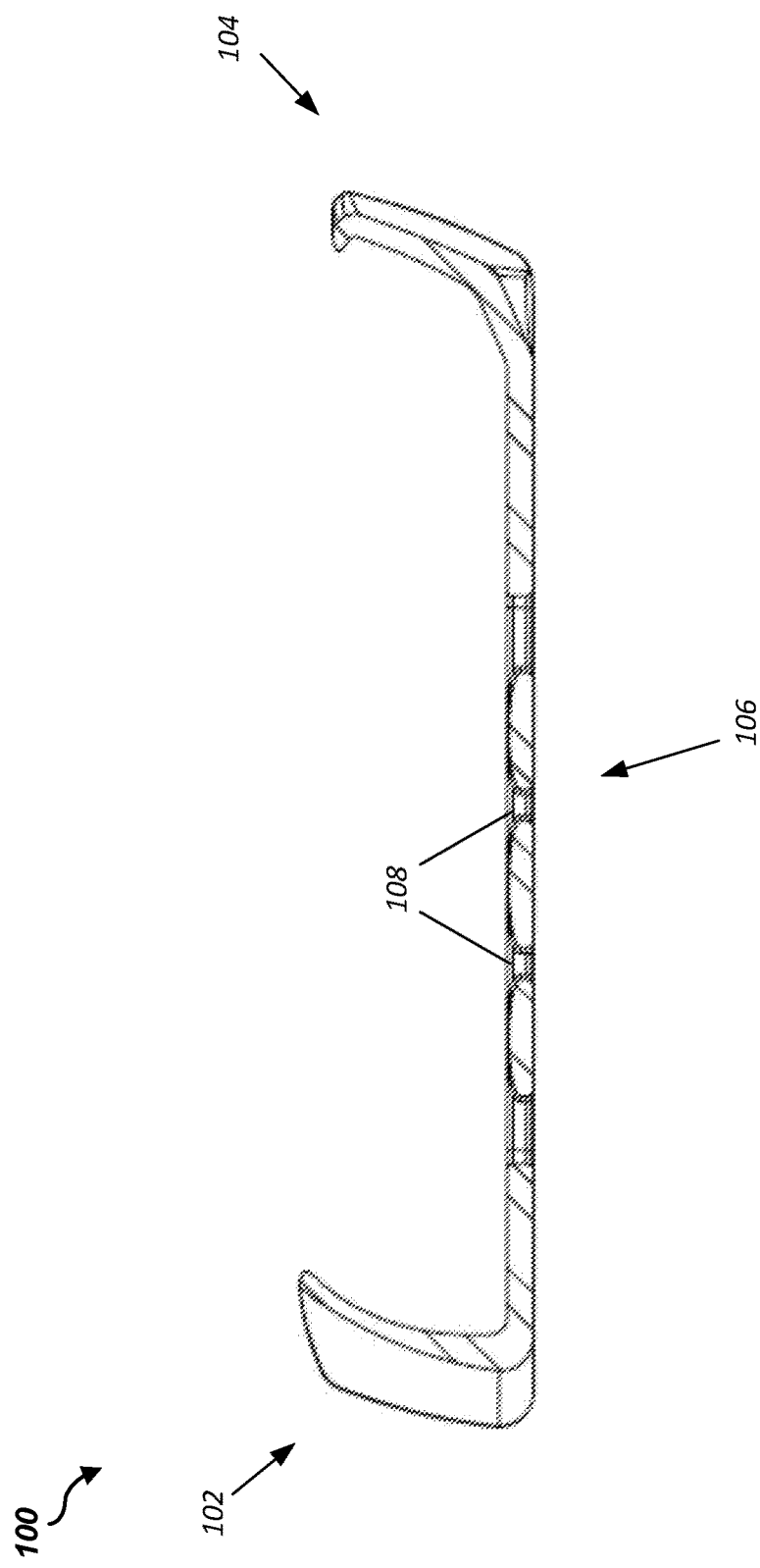
FIG. 3 is a cross-section view of the surgical retractor of FIGS. 1 and 2.

FIG. 3 shows a cross-sectional view of the retractor 100. Here, the wider end 102 of the retractor 100 has a maximum height of 1.7 inches, while the narrower end 104 extends 1.5 inches vertically. The thickness of the middle portion 106, which is largely hollow with support bars 108 disposed therein as shown, is approximately 0.18 inches.

Each of the wider end 102 and the narrower end 104 is shaped to allow for automatic toe-in when used to spread and hold flesh. In some implementations, each end 102, 104 is inclined at an angle relative to the middle portion 106 of between 25 and 30 degrees, which may be adjusted for different applications as known in the art.

Figure 4:
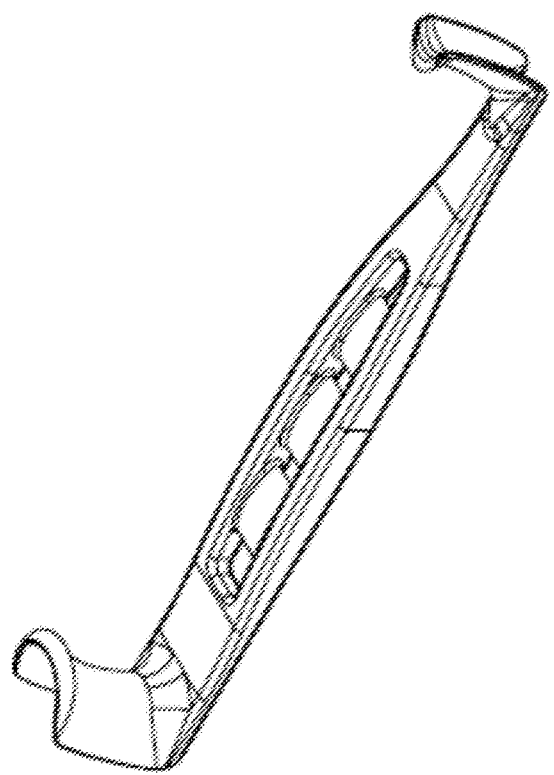
FIG. 4 is perspective view of a surgical retractor made of metal.

FIG. 4 shows a surgical retractor 200 with a structure and dimensions tailored for a construction of thermoplastic. In one implementation, the retractor 200 is made of a nylon polymer such as poly(dodecano-12-lactam), known in the art as nylon-12. Several desktop 3D printers available commercially are capable of creating durable structures using nylon-12 or its variants. The material is extruded and then hardened using selective laser sintering. Unlike the metal surgical retractor 100 described above, the plastic surgical retractor 200 may not require significant post-processing or heat treatment once the material has been sintered and allowed to set.

Notably, the retractor 200 may be made of a thermoplastic material that is transparent or translucent to medical sensing equipment, such as x-ray, MRI, CAT, and others. The retractor 200 may therefore, when necessary, remain with the patient while images are taken. Such materials, sometimes referred to in the art as 'radiolucent,' may therefore be preferable in some situations to metal, even if metal's structural characteristics are superior for the functioning of the device. MED-WHT 10 and MPU 100 are two examples of commercially available radiolucent materials. One of ordinary skill in the art will recognize that the appropriate material will depend on the intended use.

Figure 5:
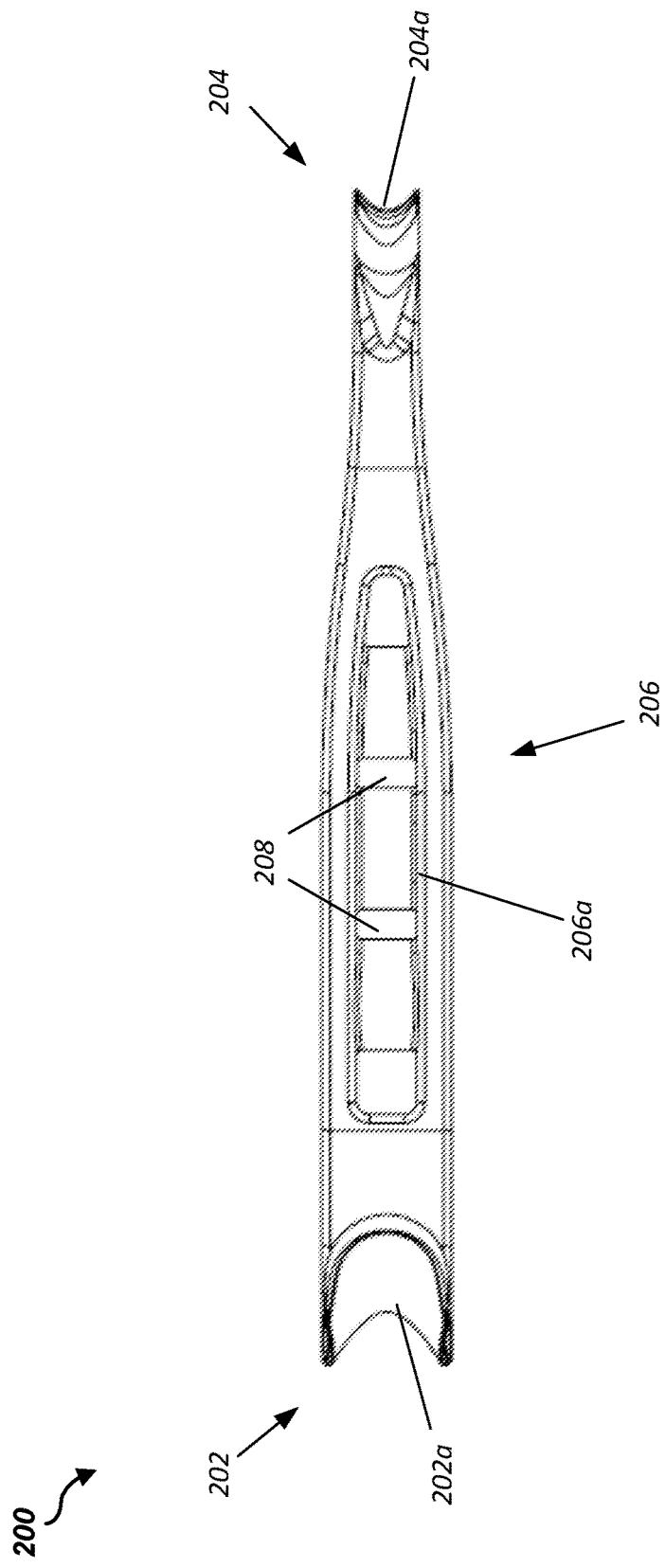
FIG. 5 is a plan view of the surgical retractor of FIG. 4.

FIG. 5 shows a plan view of the surgical retractor 200. As shown, the retractor 200 has the same length, width, and maximum height dimensions as the metal retractor 100 described above, including a wider end 202 of 1.0 inches in width, and a narrower end 204 that is 0.50 inches wide.

FIG. 6 shows a cross-sectional view of the surgical retractor 200. Here, the central section 206 is significantly thicker than the same section 106 of the metal retractor above. Its maximum thickness is approximately 0.38 inches. The dimensions of the ends 102 and 104, including their heights and inclined angles, are substantially the same as above. The differing shape and dimensions of the central portion 206 from that of the metal central portion 106 described above assures that, with the inclusion of support bars 208 as above, the retractor 200 has sufficient strength to perform its function.

The foregoing description is provided to enable any person skilled in the relevant art to practice the various embodiments described herein. Various modifications to these embodiments will be readily apparent to those skilled in the relevant art, and generic principles defined herein can be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public regardless of whether such disclosure is explicitly recited in the claims.

What is claimed is:

1. A 3D-printed surgical retractor, comprising: a main body including a hollow and a plurality of support bars; a first blade having a shaft and a hook portion inclined toward the main body, the first blade including a first groove sized and shaped to accommodate and guide a surgical device abutting the retractor; and a second blade narrower than the first blade, the second blade having a shaft and a hook portion declined away from the main body, the second blade including a second groove sized and shaped differently from the first groove, the second groove also configured to guide a surgical device abutting the retractor, said 3D-printed surgical retractor having an acute angle between said first blade's shaft and said main body, and an obtuse angle between said second blade's shaft and said main body and said first and second grooves being concave.

2. The 3D-printed surgical retractor of claim 1, wherein the retractor is a single integral piece of material produced by a 3D printer as a single integral piece.

3. The 3D-printed surgical retractor of claim 2, wherein the material is a radiolucent thermoplastic.

4. The surgical retractor of claim 1 wherein said first and second blades are inclined at an angle relative to said main body of between 25 and 30 degrees.

5. A surgical retractor, comprising: a main body including a hollow and a plurality of support bars; a first blade having a shaft and a hook portion inclined toward the main body, the first blade including a first groove sized and shaped to accommodate and guide a surgical device abutting the retractor; and a second blade narrower than the first blade, the second blade having a shaft and a hook portion declined away from the main body, the second blade including a second groove sized and shaped differently from the first groove, the second groove also configured to guide a surgical device abutting the retractor, said surgical retractor comprising metal, said surgical retractor having an acute angle between said first blade's shaft and said main body, and an obtuse angle between said second blade's shaft and said main body and said first and second grooves being concave.

6. The surgical retractor of claim 5 wherein said first and second blades are inclined at an angle relative to said main body of between 25 and 30 degrees.

\* \* \* \* \*